| United States Patent [19] | [11] Patent Number: 4,914,108 |
| Khanna et al. | [45] Date of Patent: Apr. 3, 1990 |

[54] 5-SUBSTITUTED(4,5-C)IMIDAZOPYRIDINE COMPOUNDS WHICH HAVE USEFUL PLATELET ACTIVATING FACTOR ANTAGONISTIC ACTIVITY

[75] Inventors: Ish K. Khanna, Skokie; Roger Nosal, Buffalo Grove; Richard M. Weier, Lake Bluff, all of Ill.

[73] Assignee: G. D. Searle & Co., Chicago, Ill.

[21] Appl. No.: 167,671

[22] Filed: Mar. 14, 1988

[51] Int. Cl.$^4$ .................. A61K 31/435; C07D 471/04
[52] U.S. Cl. ...................................... 514/303; 546/118
[58] Field of Search .......................... 546/118; 514/303

[56] References Cited

U.S. PATENT DOCUMENTS 4,327,100  4/1982  Austel et al. ........................ 546/118
4,336,257  6/1982  Baldwin .............................. 546/118

FOREIGN PATENT DOCUMENTS 0260613  3/1988  European Pat. Off. ............ 546/118

*Primary Examiner*—Richard A. Schwartz
*Assistant Examiner*—Zinna Northington-Davis
*Attorney, Agent, or Firm*—P. D. Matukaitis; Joy Ann Serauskas

[57] ABSTRACT

This invention relates to novel 5-substituted [4,5-c]imidazopyridine derivatives useful in the treatment of diseases or disorders mediated by platelet-activating factor. This invention also relates to pharmaceutical compositions of such substituted imidazopyradines.

53 Claims, No Drawings

5-SUBSTITUTED(4,5-C)IMIDAZOPYRIDINE COMPOUNDS WHICH HAVE USEFUL PLATELET ACTIVATING FACTOR ANTAGONISTIC ACTIVITY

BACKGROUND OF THE INVENTION

Platelet-activating factor (PAF) has been associated with various biological activities and pathway, thus making it an important mediator responsible for a variety of physiological processes including, but not limited to, activation or coagulation of platelets, smooth muscle contraction, pathogenesis of immune complex deposition, inflammation, and respiratory, cardiovascular and intravascular alterations. These physiological processes intravascular alterations. These physiological processes are associated with a large group of diseases, such as, for example, cardiovascular disorders, asthma, lung edema, endotoxin shock, adult respiratory distress syndrome and inflammatory diseases.

U.S. Pat. No. 4,804,658, discloses a class of imidazopyridine derivatives useful in the treatment of diseases or disorders mediated by platelet-activating factor. The present invention is distinct from this disclosure in that in the present invention the benzamide moiety is attached to the nitrogen (position 5) which makes up the six membered ring of the imidazopyridine ring system as opposed to the disclosure wherein the benzamide moiety is attached to one of the nitrogens which makes up the five membered ring of the imidazopyridine ring system.

SUMMARY OF THE INVENTION

The present invention relates to a novel class of compounds represented by the formula

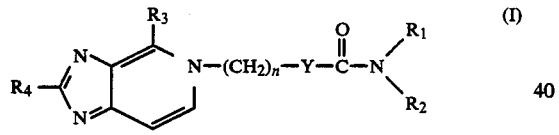

(I)

or a pharmaceutically acceptable acid addition salt thereof: wherein $R_1$ and $R_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; bicycloalkyl having 3 to 8 carbon atoms in each ring; phenyl; substituted phenyl wherein the substituent is alkyl of 1 to 6 carbon atoms or halogen; straight or branched alkenyl having 3 to 15 carbon atoms with the proviso that the double bond of the alkenyl group cannot be adjacent to the nitrogen; $R_1$ and $R_2$ cannot both be hydrogen Y is phenyl or phenyl substituted once or more than once by substituents selected from the group consisting of halogen wherein the halogen is selected from the group consisting of bromo, fluoro or chloro; alkyl of 1 to 6 carbon atoms; alkoxy wherein the alkyl is 1 to 6 carbon atoms; thioalkyl wherein the alkyl is 1 to 6 carbon atoms; alkoxyalkyl wherein the alkyl groups are each 1 to 6 carbon atoms; hydroxyalkyl wherein the alkyl is 1 to 6 carbon atoms; alkylthioalkyl wherein the alkyl group are each 1 to 6 carbon atoms; cyano; mercaptoalkyl wherein the alkyl is 1 to 6 carbon atoms; hydroxy. Substituents on the phenyl ring can be ortho, para, or meta to the connecting chain, depending on the position of the carboxamide.

n is an integer of 1 to 5

$R_3$ is hydrogen or alkyl of 1 to 6 carbon atoms $R_4$ is hydrogen or alkyl of 1 to 6 carbon atoms The invention further relates to pharmaceutical compositions comprising a compound of formula I. Such compounds and compositions have potent and specific PAF antagonistic activities and are thereby useful in the treatment of various diseases or disorders mediated by the PAF, for example inflammation, cardiovascular disorders, asthma, lung edema, and adult respiratory distress syndrome.

A preferred embodiment of the present invention are compounds of the formula

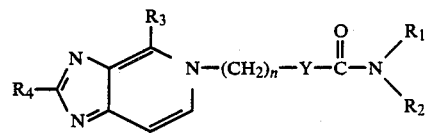

or a pharmaceutically acceptable acid addition salt thereof; wherein $R_1$ and $R_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; bicycloalkyl having 3 to 8 carbon atoms in each ring; phenyl; substituted phenyl wherein the substituent is alkyl of 1 to 6 carbon atoms or halogen; straight or branched alkenyl having 3 to 15 carbon atoms with the proviso that the double bond of the alkenyl group cannot be adjacent to the nitrogen; $R_1$ and $R_2$ cannot both be hydrogen Y is phenyl;

n is an integer of 1 to 5

$R_3$ is hydrogen or alkyl of 1 to 6 carbon atoms $R_4$ is hydrogen or alkyl of 1 to 6 carbon atoms A further embodiment of the present invention are compounds of the formula

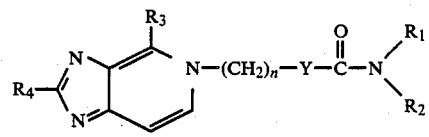

or a pharmaceutically acceptable acid addition salt thereof; wherein $R_1$ and $R_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; bicycloalkyl having 3 to 8 carbon atoms; phenyl; substituted phenyl wherein the substituent is alkyl of 1 to 6 carbon atoms or halogen; with the proviso that $R_1$ and $R_2$ cannot both be hydrogen Y is substituted phenyl wherein the substituent is halogen selected from the group consisting of bromo fluoro or chloro or alkoxy wherein the alkyl is 1 to 6 carbon atoms; Substituents on the phenyl ring can be ortho, para, or meta to the connecting chain, depending on the position of the carboxamide.

n is an integer of 1 to 3

$R_3$ is hydrogen or alkyl of 1 to 6 carbon atoms $R_4$ is hydrogen or alkyl of 1 to 6 carbon atoms As used herein the term "alkyl of 1 to 15 carbon atoms": refers to straight chain or branched chain hydrocarbon groups having from one to fifteen carbon atoms. Illustrative of such alkyl groups are methyl, ethyl, propyl isopropyl, butyl, isobutyl, pentyl, neopentyl, hexyl, isohexyl, octyl, decyl and the like.

As used herein the term "cycloalkyl having 3 to 8 carbon atoms" included cycloalkyl groups having from three to eight carbons. Illustrative of such cycloalkyl groups are cyclopropyl, cyclobutyl, cyclopentyl, cyclohexyl, cycloheptyl, cyclooctyl and the like.

As used herein the term halogen includes fluoro, chloro and bromo.

As used herein the term "alkenyl having 2 to 15 carbon atoms" refers to straight or branched unsaturated hydrocarbon groups having from 3 to 15 carbon atoms. Illustrative of such alkenyl groups are 2-propenyl, hexenyl, octenyl, decenyl and the like.

As used herein the term "alkoxy wherein the alkyl is 1 to 6 carbon atoms" refers to straight or branched chain ethers. Illustrative of such groups are methoxy, ethoxy, propoxy, butoxy, isopropoxy and the like.

The term "pharmaceutically acceptable acid addition salt" refers to a salt prepared by contacting a compound of formula (I) with an acid whose union is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

The compounds of formula (I) may be prepared in accordance with the following procedures.

Imidazopyridine which is represented by the following formula

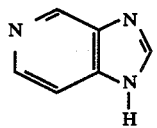

II is reacted with a haloalkylbenzamide which is represented by the following formula

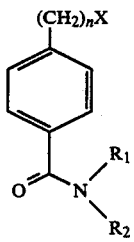

III wherein $R_1$ and $R_2$ and n are defined as before and X is bromo, or methanesulfonyloxy to give the compounds of formula I. It is understood that the haloalkylbenzamide can also be substituted by halogen, alkyl of 1 to 6 carbon atoms; alkoxy wherein the alkyl is 1 to 6 carbon atoms; thioalkyl wherein the alkyl is 1 to 6 carbon atoms; alkoxy alkyl wherein the alkyl is 1 to 6 carbon atoms; hydroxyalkyl wherein the alkyl is 1 to 6 carbon atoms; alkylthioalkyl wherein the alkyl is 1 to 6 carbon atoms; cyano; mercaptoalkyl wherein the alkyl is 1 to 6 carbon atoms; hydroxy.

Preferred reaction conditions for the above-identified procedure include heating overnight at 70°-90° C. a solution of haloalkylbenzamide and imidazopyridine in a solvent such as dimethylacetamide (approximately 0.1M in each). After heating overnight the reaction solvent was removed in vacuo and the residue diluted with water and basified with ammonium hydroxide. The aqueous solution was extracted with chloroform and the combined organic extracts were backwashed with saturated aqueous sodium chloride solution. The organic solution was dried over sodium sulfate or magnesium sulfate, the drying agent filtered and the filtrate concentrated in vacuo to give the crude product. Purification was effected by chromatography on silica gel using mixtures of chloroform, ethanol and ammonium hydroxide.

An alternate work up for the above-described procedure is to cool the reaction solution which had been heated overnight to room temperature and remove the solvent under reduced pressure at <45° C. The residue obtained was triturated with excess of dry ether and filtered. The crude product was purified by chromatography.

Scheme A

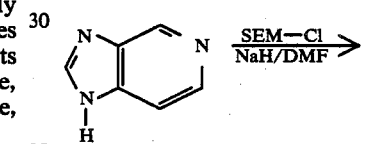

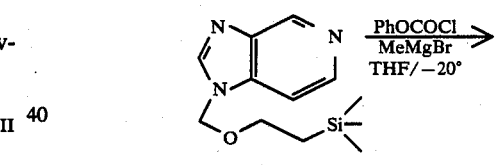

1

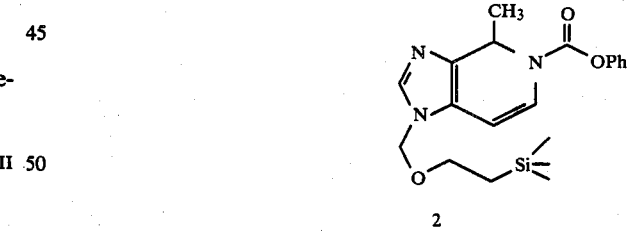

2

1. EtOH—NaOH
2. Chloranil

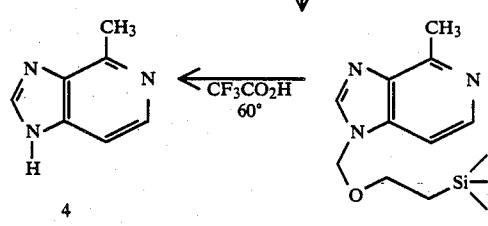

4        3

The imidazo [4,5-c]pyridine wherein $R_3$ is methyl was prepared according to the scheme above starting with the imidazopyridine of Formula II. Position 1 of this compound was protected by reaction with a 2-(trialkylsilyl) ethoxy methyl chloride and a base such as sodium hydride or potassium hydride in a polar aprotic solvent such as dimethylformamide. This reaction was carried out at room temperature. A specific example of such a protecting group was 2-(trimethylsilyl)ethoxymethyl chloride. The protected imidazopyridine was reacted with phenyl chloroformate and methylmagnesium bromide in an ether solvent such as tetrahydrofuran at about $-20°$ C. The methylated product bearing phenoxycarbonyl at position 5 was treated with a base, such as alcoholic sodium hydroxide, at reflux for 24 hr. The product was oxidized with, for example, chloranil, and the 2-(trimethylsilyl)ethoxymethyl group was removed by treatment with a suitable acid. An example of such an acid would be trifluoroacetic acid. Preparation of the unsubstituted imidazo [4,5-c] pyridine is described in U.S. Pat. No. 4,804,658.

The haloalkyl benzamides are prepared according to the following reaction scheme

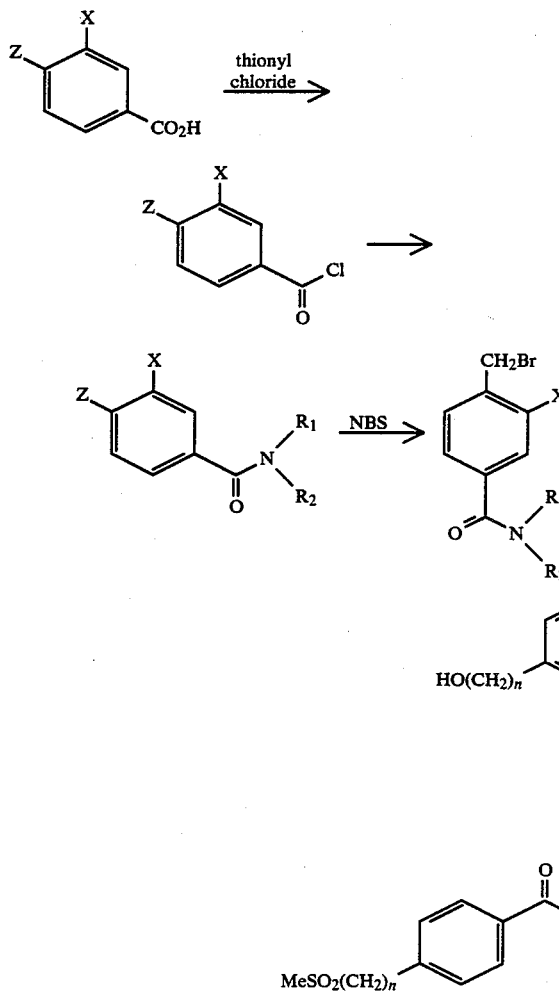

wherein $R_1$ and $R_2$ are defined as before; Z is $CH_3CH_2Br$ or H; X is fluoro, OMe or methyl Thus according to the above scheme the acid chlorides were prepared from the corresponding carboxylic acids by refluxing in thionyl chloride (2 molar excess) for two hours. Excess thionyl chloride was removed by azeotrope with toluene. The residual acid chloride was dissolved in THF and cooled to $-10°$ C. A solution of two molar equivalents of the secondary amine in the THF was added dropwise with stirring. When addition was completed, the reaction was allowed to warm to room temperature and stirred for 1-2 hours. The reaction was quenched with 1N HCL, diluted with $H_2O$ and extracted three times with ethyl acetate. The combined organic layers were washed with saturated aqueous sodium bicarbonate solution, with water and with saturated aqueous sodium chloride and dried over sodium sulfate. The drying agent was filtered and the filtrate concentrated in vacuo to give a crude product that was chromatographed on silica gel using mixtures of ethyl acetate and hexane to give the purified amide.

When $Z=CH_2Br$ and $X=H$, the above description is sufficient for the preparation of the compounds of Formula III. When $Z=CH_3$, and $X=OMe$ or F, or when $Z=H$ and $X=CH_3$ then compound of Formula VI must be treated with a halogenating agent such as N-bromo succinimide.

A stirred mixture of the purified amide and NBS (1:1 molar ratio) in carbon tetrachloride was irradiated with a sun lamp for 1-3 hours. A white precipitate was filtered and washed with a minimum amount of $CHCl_3$. The filtrate was washed with water and the aqueous layer, after basification with ammonium hydroxide, was extracted three times with chloroform. All organic layers were combined, washed three times with saturated aqueous sodium chloride solution and dried over sodium sulfate.

The drying agent was filtered and the filtrate concentrated in vacuo to give a crude product that was chromatographed on silica gel using mixtures of ethyl acetate and hexane to give the purified bromomethyl compound.

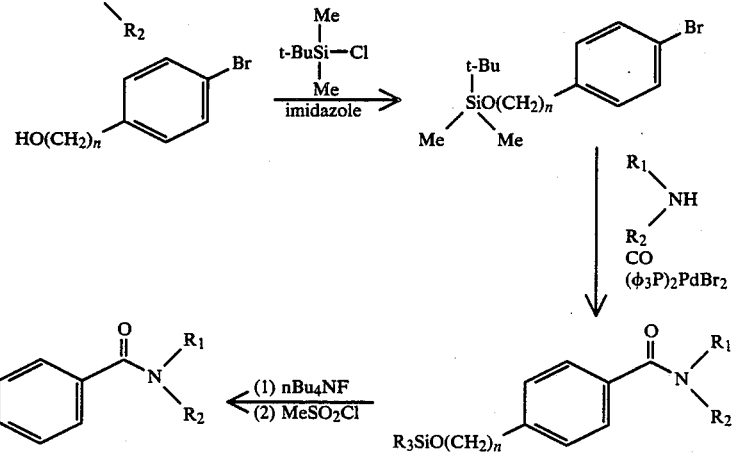

The benzamides wherein $n=2$ or 3 can be prepared according to the scheme above starting with the appropriate hydroxyalkyl bromobenzene. The hydroxyl group was protected as a trialkylsilyl ether by reaction with a trialkylsilyl chloride and imidazole in a suitable solvent such as dimethylformamide. An example of such a protecting group would be the t-butyldimethylsilyl ether. The crude silyl ether was purified by chromatography on silica gel using mixtures of ethyl acetate and hexane. The aryl bromide was converted to the carboxamide according to the procedure of Schoenberg et al. [J. Org. Chem., 39, 3327(1974)]. Thus, the aryl bromide was reacted with carbon monoxide in the secondary amine as solvent using bistriphenylphosphine palladium(II) dibromide as catalyst at about 100° C. for 8-26 hr. in a pressure vessel. The reaction vessel was vented, the reaction mixture triturated with ethyl ether and the washings filtered. The filtrate was washed with 10% aqueous HCl, water and brine. After drying over a suitable drying agent, such as magnesium sulfate, and filtering, the filtrate was concentrated and the residue chromatographed on silica gel using mixtures of ethyl acetate and hexane as eluent to give pure product. The silyl ether was removed by reaction with tetra-n-butylammonium fluoride and the alcohol was converted to a sulfonate ester by reaction with an alkyl or arylsulfonyl chloride. An example of such a sulfonate would be the methanesulfonate.

The secondary amines may be prepared by any number of methods known to those skilled in the art. See references Emerson, W. S. Org. Reactions 4, 174 1948)

J. B. Cambell, L. B. Lavaginino in "Catalysis in Organic Synthesis" (Jones W. H., ed.) p. 43, Academic Press, New York, 1980.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Dosage levels of the order from about 1 mg to about 100 mg per kilogram of body weight per day are useful in the treatment of the above-indicated conditions (from about 50 mg to about 5 mgs. per patient per day). For example, inflammation is effectively treated and antipyretic and analgesic activity manifested by the administration from about 25 to about 75 mg of the compound per kilogram of body weight per day (about 75 mg to about 3.75 gm per patient per day). Preferably, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 95 mg of active agent compounded with an appropriate and convenient amount of carrier material which may vary from about 5 to 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. The following Examples are intended to further illustrate the present invention and not to limit the invention in spirit or scope. In the Examples, all parts are parts by weight unless otherwise expressly set forth.

EXAMPLE 1

5-[4-(N-methyl-N-cyclohexylcarboxamido)benzyl-]imidazo[4,5-c]pyridine

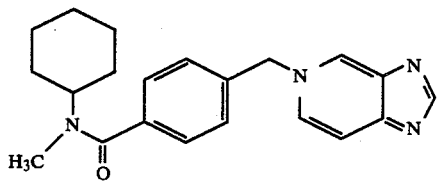

To a stirred solution of imidazopyridine (5.86 g, 49.2 mmol) in DMF (125 ml) under a nitrogen atmosphere was added washed, dried sodium hydride (prepared from 3.54 g of 50% dispersion in oil by washing four times with 50–75 ml portions of hexane). After stirring for 1 hr. at room temperature, the evolution of hydrogen gas had ceased and the reaction was cooled to −10° C. N-Methyl-N-cyclohexyl-α-bromo-p-toluyl amide (16.9 g, 54.5 mmol) was added. The reaction was stirred at 0° for 45 min. and at room temperature for 3 hrs.

DMF was removed in vacuo and the residue was diluted with $H_2O$ (200 ml) and the resulting solution was saturated with sodium chloride. The aqueous solution was extracted four times with ethyl acetate (100 ml portions) and the combined organic layers were washed three times with saturated aqueous sodium chloride solution (150 ml portions). After drying over sodium sulfate, the organic solution was filtered and concentrated in vacuo to give 13.38 g of crude product as a brown gum. This material was chromatographed on silica gel using ethanol/chloroform/ammonium hydroxide (20/79/1) to give 3.13 g of compound as an orange oil that crystallized on treatment with ethyl acetate. Recrystallization from ethyl acetate yielded 1.06 g.

Analysis Calcd for $C_{21}H_{24}N_4O \cdot \frac{1}{4}H_2O$: C, 71.46; H, 7.00; N, 15.88. Found: C, 71.14; H, 7.18; N, 15.78. m.p. 115–17° C.

EXAMPLE 2

5-[4-(N-methyl-N-cyclohexylcarboxamido)-2-fluorobenzyl]imidazo[4,5-c]pyridine

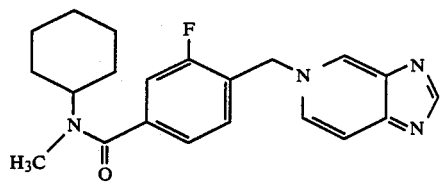

A solution of N-methyl, N-cyclohexyl 3-fluoro 4-bromomethyl benzamide (1.2 g, 2.66 mm) and imidazopyridine (0.48 g, 4.0 mm) in dimethyl acetamide (25 ml) was heated overnight at 70–80° C. with stirring under $N_2$. Reaction solvent was removed in vacuo and the residue diluted with water and basified with ammonium hydroxide. The aqueous solution was extracted four times with chloroform and the combined organic extracts were backwashed three times with saturated aqueous sodium chloride solution. The organic solution was dried over magnesium sulfate, the drying agent was filtered and the filtrate concentrated in vacuo to give 0.88 g of the crude compound. Purification of the compound was effected by chromatography on silica using mixtures of chloroform, ethanol and ammonium hydroxide.

Analysis calcd for $C_{21}H_{23}FN_4O \cdot O.8\ H_2O$: C,66.22; H, 6.51; N, 14.71; F,4.99. Found: C, 66.03; H, 6.44; N, 14.65; F,4.91. mp 154–158° C.

In the same manner as described in Example 2 the compounds of the Examples 3 to 11 described in Tables A & B were prepared.

TABLE A

| Example | R₁ | R₂ | X | n | R₃ | R₄ | mpt. (°C.) | Analysis Calcd | Found | Mol. Formula |
|---|---|---|---|---|---|---|---|---|---|---|
| 3 | cyclopentyl | cyclopentyl | OCH₃ | 1 | H | H | 217-19 | C: 71.12<br>H: 7.26<br>N: 13.28 | 70.83<br>7.33<br>13.06 | $C_{25}H_{30}N$ |
| 4 | cyclohexyl | cyclopentyl | OCH₃ | 1 | H | H | 197-99 | C: 71.01<br>H: 7.52<br>N: 12.74 | 70.87<br>7.49<br>12.70 | $C_{26}H_{32}N_4O$<br>$0.4H_2O$ |
| 5 | cyclohexyl | isopropyl | OCH₃ | 1 | H | H | 192-95 | C: 70.90<br>H: 7.44<br>N: 13.78 | 70.15<br>7.47<br>13.71 | $C_{24}H_{30}N_4O$ |
| 6 | cyclohexyl | CH₃ | OCH₃ | 1 | H | H | 206-8° | C: 69.15<br>H: 6.86<br>N: 14.67 | 68.78<br>6.88<br>14.57 | $C_{22}H_{26}N_4O$<br>$0.2H_2O$ |
| 7 | cyclohexyl | cyclopentyl | F | 1 | H | H | 205-8 | C: 71.4<br>H: 6.95<br>N: 13.33<br>F: 4.52 | 71.11<br>7.11<br>13.16<br>4.30 | $C_{25}H_{29}FN_4O$ |
| 8 | cyclohexyl | isopropyl | F | 1 | H | H | 178-82 | C: 68.46<br>H: 6.99<br>N: 13.89<br>F: 4.71 | 68.46<br>6.71<br>13.45<br>4.38 | $C_{23}H_{27}FN_4$<br>$0.5H_2O$ |
| 9 | cyclohexyl | CH₃ | F | 1 | H | H | 154-8 | C: 66.22<br>H: 6.51<br>N: 14.71<br>F: 4.99 | 66.03<br>6.44<br>14.65<br>4.91 | $C_{21}H_{23}N_4F$<br>$0.8H_2O$ |

TABLE B

| Example | R₁ | R₂ | mpt. (°C.) | Analysis Calcd | Found | Mol. Formula |
|---|---|---|---|---|---|---|
| 10 | cyclopentyl | —CH₃ | 167-69 | C: 72.38<br>H: 6.94<br>N: 16.08 | 72.26<br>7.10<br>16.01 | $C_{21}H_{24}N_4O$ |
| 11 | cyclohexyl | isopropyl | 207-12° | C: 73.37<br>H: 7.50<br>N: 14.88 | 72.97<br>7.63<br>14.61 | $C_{23}H_{28}N_4O$ |

EXAMPLE 12

5-[(4-(N,N-dicyclohexylcarboxamido)benzyl-]imidazo[4,5-c]pyridine pyridine

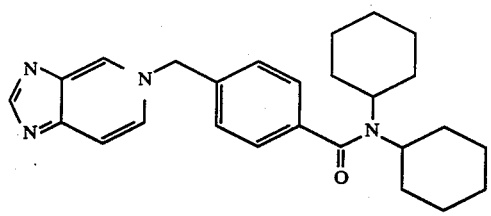

To a stirred solution of imidazopyridine (750 mg, 6.3 mmol) in N,N-dimethylacetamide, 4-bromomethyl-N,N-dicyclohexyl benzamide (2.6 g, 6.88 mmol) was added. The reaction mixture was stirred under argon at 80°–85° C. After 24 h, the reaction flask was cooled to room temperature and the solvent removed under reduced pressure at <45° C. The residue obtained was triturated with ether (2×70 mL) and filtered. The crude (2.7 g) was chromatographed (silica gel, $CH_2Cl_2$—MeOH—$NH_4OH$ 80-20-1) to give pure product (1.47 g, 62%) which was recrystallized from EtOAc—$CH_3CN$. mp 233°–35° C.; $C_{26}H_{32}N_4O$. $0.3H_2O$: C, 74.0: H, 7.73: N, 13.28 Found C, 73.93; H, 7.90; N, 13.09.

In the same manner as described in Example 12 the compounds of the Examples 13 to 38 described in Table C were prepared.

TABLE C

| Example | $R_1$ | $R_2$ | X | n | $R_3$ | $R_4$ | mpt. (°C.) | Analysis Calcd. | Found | Mol. Formula |
|---|---|---|---|---|---|---|---|---|---|---|
| 13 | cyclohexyl | $CH_3$ | H | 1 | H | H | 115–17 | C: 71.46<br>H: 7.00<br>N: 15.88 | 71.14<br>7.18<br>15.78 | $C_{21}H_{24}N_4O$<br>$0.25H_2O$ |
| 14 | —$(CH_2)_7CH_3$ | H | H | 1 | H | H | 113–15 | C: 72.52<br>H: 7.69<br>N: 15.38 | 72.26<br>7.72<br>15.28 | $C_{22}H_{28}N_4O$ |
| 15 | —$(CH_2)_9CH_3$ | H | H | 1 | H | H | 141–45 | C: 73.46<br>H: 8.16<br>N: 14.28 | 73.35<br>8.32<br>14.26 | $C_{24}H_{32}N_4O$ |
| 16 | cyclohexyl | isopropyl | H | 1 | H | H | 209–10 | C: 72.70<br>H: 7.48<br>N: 14.75 | 72.92<br>7.60<br>14.82 | $C_{23}H_{28}N_4O$<br>$0.2H_2O$ |
| 17 | cyclohexyl | isobutyl | H | 1 | H | H | 210–11° | C: 73.80<br>H: 7.69<br>N: 14.35 | 73.40<br>7.78<br>14.25 | $C_{24}H_{30}N_4O$ |
| 18 | —$(CH_2)_{11}CH_3$ | H | H | 1 | H | H | 150–2 | C: 74.28<br>H: 8.57<br>N: 13.33 | 74.10<br>8.75<br>13.36 | $C_{26}H_{36}N_4O$ |
| 19 | decahydronaphthyl | H | H | 1 | H | H | 113–28 | C: 73.31<br>H: 7.52<br>N: 13.68 | 73.41<br>7.79<br>13.38 | $C_{25}H_{30}N_4O$<br>$0.4H_2O$ |
| 20 | neopentyl | H | H | 1 | H | H | 221–2 | C: 72.52<br>H: 7.69<br>N: 15.38 | 72.33<br>7.82<br>15.28 | $C_{22}H_{28}N_4O$ |
| 21 | cyclohexyl | $CH_3$ | H | 2 | H | H | 223–5 | C: 71.15<br>H: 7.27<br>N: 15.09 | 70.79<br>7.48<br>14.81 | $C_{22}H_{26}N_4O$<br>$0.5H_2O$ |
| 22 | cyclohexyl | $CH_3$ | H | 3 | H | H |  | C: 70.86<br>H: 7.57<br>N: 14.36 | 70.82<br>7.64<br>14.23 | $C_{23}H_{28}N_4O$<br>$0.75H_2O$ |

TABLE C-continued

Structure: imidazo[4,5-c]pyridine with R3, R4 substituents, N-(CH2)n linker to benzene with X substituent and C(=O)N(R1)(R2) group.

| Example | R1 | R2 | X | n | R3 | R4 | mpt. (°C.) | Analysis Calcd. | Found | Mol. Formula |
|---|---|---|---|---|---|---|---|---|---|---|
| 23 | cyclopentyl | cyclopentyl | H | 1 | H | CH₃ | 197–98 | C: 74.62<br>H: 7.46<br>N: 13.93 | 74.24<br>7.50<br>13.80 | C₂₅H₃₀N₄O |
| 24 | cyclopentyl | cyclopentyl | H | 1 | CH₃ | H | 225–8° | C: 72.31<br>H: 7.48<br>N: 13.18 | 72.36<br>7.57<br>13.50 | C₂₅H₃₀N₄O · 0.7H₂O |
| 25 | cyclohexyl | cyclobutyl | H | 1 | H | H | 190–3 | C: 74.22<br>H: 7.21<br>N: 14.43 | 73.98<br>7.27<br>14.33 | C₂₄H₂₈N₄O |
| 26 | cyclohexyl | cyclopentyl | H | 1 | H | H | 222–23 | C: 74.62<br>H: 7.46<br>N: 13.93 | 74.21<br>7.45<br>14.26 | C₂₅H₃₀N₄O |
| 27 | cyclohexyl | cyclohexyl | H | 1 | H | H | 233–35 | C: 74.0<br>H: 7.73<br>N: 13.28 | 73.93<br>7.90<br>13.07 | C₂₆H₃₂N₄O · 0.3H₂O |
| 28 | cyclohexyl | tert-butyl | H | 1 | H | H | 197–98 | C: 73.84<br>H: 7.69<br>N: 14.35 | 73.86<br>7.87<br>14.35 | C₂₄H₃₀N₄O |
| 29 | phenyl | cyclopentyl | H | 1 | H | H | 213–14 | C: 75.73<br>H: 6.10<br>N: 14.13 | 75.66<br>6.18<br>14.08 | C₂₅H₂₄N₄O |
| 30 | 3-methylcyclohexyl | cyclopentyl | H | 1 | H | H | 187–89 | C: 74.94<br>H: 7.74<br>N: 13.44 | 74.58<br>7.84<br>13.32 | C₂₆H₃₂N₄O |
| 31 | 4-methylcyclohexyl | cyclopentyl | H | 1 | H | H | 211–12 | C: 74.94<br>H: 7.74<br>N: 13.44 | 74.85<br>7.84<br>13.39 | C₂₆H₃₂N₄O |
| 32 | cyclohexyl | isobutyl | H | 1 | H | H | 198–200 | C: 73.84<br>H: 7.69<br>N: 14.35 | 73.20<br>7.70<br>14.74 | C₂₄H₃₀N₄O |
| 33 | cyclohexyl | isopentyl | H | 1 | H | H | 211–13 | C: 73.60<br>H: 7.85<br>N: 13.73 | 73.12<br>7.92<br>13.72 | C₂₅H₃₂N₄O · 0.2H₂O |

TABLE C-continued

| Example | R$_1$ | R$_2$ | X | n | R$_3$ | R$_4$ | mpt. (°C.) | Analysis Calcd. | Found | Mol. Formula |
|---|---|---|---|---|---|---|---|---|---|---|
| 34 | cyclohexyl | cyclopropyl | H | 1 | H | H | 88–90 | C: 72.06<br>H: 7.04<br>N: 14.62 | 72.25<br>7.16<br>14.48 | C$_{23}$H$_{26}$N$_4$O<br>0.5H$_2$O |
| 35 | isopropyl | isopropyl | H | 1 | H | H | 224–5 | C: 71.42<br>H: 7.14<br>N: 16.66 | 71.30<br>7.29<br>16.71 | C$_{20}$H$_{24}$N$_4$O |
| 36 | cyclopentyl | cyclopentyl | H | 1 | H | H | 228–30 | C: 74.22<br>H: 7.21<br>N: 14.43 | 74.04<br>7.29<br>14.28 | C$_{24}$H$_{28}$N$_4$O |
| 37 | cyclohexyl | H | H | 1 | H | H | 219–21 | C: 70.33<br>H: 6.68<br>N: 16.41 | 70.34<br>6.87<br>16.28 | C$_{20}$H$_{22}$N$_4$O<br>0.4H$_2$O |
| 38 | cyclohexyl | —CH$_2$CH$_3$ | H | 1 | H | H | 156–8 | C: 71.85<br>H: 7.24<br>N: 15.24 | 71.85<br>7.24<br>15.19 | C$_{22}$H$_{26}$N$_4$O<br>0.3H$_2$O |

EXAMPLE 39

PAF-induced platelet aggregation and secretion: Washed, [$^3$H]serotonin-labeled rabbit platelets were prepared as previously described in COX, C. P., J. LINDEN and S. I. SAID: VIP elevates platelet cyclic AMP (cAMP) levels and inhibits in vitro platelet activation induced by platelet-activating factor (PAF). Peptides 5:25–28, 1984, and maintained in an atmosphere of 5% CO$_2$ at 37° C. until used in the bioassay. Aliquots of platelets (2.5×10$^8$/ml) were incubated with either an antagonist of PAF or the appropriate vehicle for 60 sec prior to the addition of PAF (0.2 nM to 0.2 µM). Aggregation was continuously monitored on a strip-chart recorder and recorded as the height of the tracing at 60 sec after the the addition of PAF. Secretion of [$^3$H] serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated 12–15 times, using several different platelet preparations. IC$_{50}$ values were determined by inspection of the dose-response curves.

EXAMPLE 40

Inhibition of $^3$H-PAF Binding to Human Platelet Membrane Receptors

Receptor Preparation: Ten units of in-dated human packed platelets, each containing 45–65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM (2300×g). Plasma was decanted and the platelets were resuspended in 35 ml of buffer (10 mM Trizma 7.0, 2 mM EDTA (dipotassium salt), and 150 mM KCl) and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM CaCl$_2$. Following centrifugation, the buffer was decanted and the pellets were resuspended in the CaCl$_2$ buffer, avoiding erythrocyte contamination by recovering less than 100% of the platelet pellets. The resuspended platelets were dispensed in 8–10 ml aliquots into Corex tubes and disrupted by three cycles of freezing (dry ice/ethanol) and thawing (24° C.) The tubes were centrifuged at 40,000×g for 20 minutes at 4° C. Supernatants were decanted and each pellet was resuspended in 5–7 ml 10 mM Trizma 7.0. All resuspended pellets were pooled and aliquots of about 1200 µl were dispensed into 1.5 ml microfuge tubes and frozen at −70° C. Protein content was determined by a fluorescamine protein assay.

Assay Methods: Receptor Characterization—Each receptor preparation was evaluated to determine the number of receptor populations, the number of PAF receptor equivalents/mg protein and the dissociation constant (K$_D$) for PAF binding. This required 2–3 experiments in which the protein concentration was held constant and the $^3$H-PAF ligand concentration was varied from approximately 0.10–2.5 nM and the data was analyzed by Scatchard methodology. Total incubation volume was 250 μl for these procedures and incubations were conducted at 24° C. for 30 minutes. For further experimentation, total incubation volumes are 500 μl. Protein and ligand concentrations were adjusted to give 0.075 nM receptor equivalents in the presence of 0.75 nM $^3$H-PAF. Each receptor preparation was then used to determine the dose - response displacement relationship of unlabeled PAF and the PAF antagonist, triazolam. As long as the $K_D$ value and $IC_{50}$ values for PAF and triazolam were consistent with similar data collected from past receptor preparations used in the assay, the new receptor preparation was used for evaluating compounds.

Assay Methods: Routine Assay of Compounds—The compounds were weighed precisely and solubilized in quantities of DMSO such that a 5 μl aliquot in the incubate would deliver the desired compound concentration. Compounds tested for the first time in this assay were evaluated at a concentration of 50 μM in the incubation medium. All compounds were generally solubilized in DMSO for about 2 hours prior to assay. Triazolam was always included in each screening assay as a compound inhibition control. A standard concentration of 50 μM inhibited $^3$H-PAF binding by approximately 50%. Nonspecific binding control solution was made by drying to completion about 26.2 μl unlabeled PAF under a stream of argon. PAF was resolubilized in 1000 μl DMSO. When delivered in a 5 μl aliquot, the final concentration of 1 μM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM CaCl$_2$). Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 μl of stock $^3$H-PAF (DuPont NEN, NET-668) to 14 ml of assay buffer. Since the amount of $^3$H-PAF in the final incubate was to be 0.75 nM, the actual amount of stock $^3$H-PAF to be used had to be determined for each lot of material based upon its specific activity.

Membrane receptors for assay were prepared by thawing the appropriate number of tubes at room temperature and adding membranes to 10 mM Trizma 7.0 containing 10 mM CaCl$_2$. A total volume of 14 ml was made. The actual amount of membranes needed was determined by the requirement to have 0.075 nM PAF receptor equivalents per assay tube. All materials were kept in motion by rocking on a rocker plate.

First, 5 μl of compound or DMSO was added to each 12×75 mm polypropylene tube, followed by the addition of 95 μl assay buffer. Next, 200 μl $^3$H-PAF was added to each tube and 3 aliquots of $^3$H-PAF taken at different times during the dispensing were placed in scintillation vialsN The reaction was initiated by the addition of 200 μl of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 μl total volume of incubate. This consisted of 5 μl drug with DMSO or only DMSO, 95 μl assay buffer, 200 μl $^3$H-PAF (0.75 nM final concentration) and 200 microliters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 μM, or to run dose-response determinations for a compound. In general, dose-response curves were composed of 4 compound doses designed to inhibit $^3$H-PAF binding by 15-85%, with at least 1 dose on each side of the 50% point.

Routine Assay Calculations: Triplicate DPM determinations (corrected for background) within a single compound dose were averaged while all 6 determinations of total binding ("0" dose, DMSO only) were averaged. The amount for nonspecific binding (1 μM PAF) was subtracted from all the dose averages, giving an amount of specific binding in all cases. The percent displacement of $^3$H-PAF or inhibition of binding was calculated by the formula $STB_o$-$SB_c$/$STB_o$ × 100, where $STB_o$=specific binding of "0" dose controls and $SB_c$=specific binding in the presence of compound. If a compound tested at the initial screening dose of 50 μM inhibited binding by 45% or more, the compound was considered active and was tested in a dose-response manner to determine an $IC_{50}$ value. Compounds inhibiting PAF binding by less than 45% at a 50 μM concentration were considered inactive and no further testing was done.

$IC_{50}$ values were determined on active compounds in subsequent tests. Three or more compound doses must inhibit $^3$H-PAF binding between 15-85%. Using a computer program, % displacement data was transformed (logit) and a least squares linear regression was performed on the data meeting the 15-85% requirement to determine $IC_{50}$ values from data points derived from the same assay.

| Compound | PAF induced platelet secretion $(IC_{50})M$ | PAF induced platelet aggregation $(IC_{50})M$ | Inhibition of $^3$H-PAF Binding to Human Platelet $(IC_{50})\mu M$ |
|---|---|---|---|
| 5-[4-(N-methyl-N-cyclohexylcarboxamido)benzyl]imidazo[4,5-c]pyridine | $7.2 \times 10^{-7}$ | $10^{-5}$ to $10^{-6}$ | 15.2 |
| 5-[4-(N-n-octylcarboxamido)benzyl]imidazo[4,5-c]pyridine | $10^{-6}$ to $10^{-7}$ | $10^{-5}$ to $10^{-6}$ | 11.0 |

-continued

| Compound | PAF induced platelet secretion (IC$_{50}$)M | PAF induced platelet aggregation (IC$_{50}$)M | Inhibition of $^3$H-PAF Binding to Human Platelet (IC$_{50}$)μM |
|---|---|---|---|
| 5-[4-(N-n-decylcarboxamido)benzyl]imidazo[4,5-c]pyridine | $10^{-6}$ to $10^{-7}$ | $10^{-5}$ to $10^{-6}$ | 9.71 |
| 5-[4-(N-n-dodecylcarboxamido)benzyl]imidazo[4,5-c]pyridine | 1 to 5 × $10^{-7}$ | $10^{-6}$ to $10^{-7}$ | 11.9 |
| 5-[4-(N-2-decalyl-N-methylcarboxamido)benzyl]imidazo[4,5-c]pyridine | $10^{-6}$ | $10^{-5}$ to $10^{6}$ | 13.2 |
| 5-[4-(N-2(2,4,4-trimethyl)pentylcarboxamido)benzyl]imidazo[4,5-c]pyridine | $10^{-6}$ | $10^{-5}$ | 22.3 |
| 5-[4-(N,N-diisopropyl carboxamido)benzyl]imidazo[4,5-c]pyridine | $10^{-7}$ to $10^{8}$ | $10^{-5}$ to $10^{-6}$ | 7.65 |
| 5-[4-(N,N-dicyclopentyl carboxamido)benzyl]imidazo[4,5-c]pyridine | $10^{-8}$ to $10^{-9}$ | $10^{-7}$ to 5 × $10^{-8}$ | 0.31 |
| 5-[4-(N-cyclohexylcarboxamido)benzyl]imidazo[4,5-c]pyridine | $10^{-6}$ to $10^{-7}$ | $10^{-5}$ | 19.3 |
| 5-[4-(N-ethyl-N-cyclohexyl carboxamido)carboxamido)benzyl]imidazo[4,5-c]pyridine | $10^{-7}$ to $10^{-6}$ | $10^{-6}$ to $10^{-5}$ | 5.20 |
| 5-[4-(N-isopropyl-N-cyclohexyl carboxamido)benzyl]imidazo[4,5-c]pyridine | $10^{-8}$ | $10^{-7}$ to $10^{-8}$ | 0.17 |
| 5-[4-(N-sec.butyl-N-cyclohexylcarboxamido)benzyl]imidazo[4,5-c]pyridine | $10^{-8}$ to $10^{-9}$ | $10^{-7}$ to 5 × $10^{-8}$ | 0.58 |
| 5-[4-(N-isobutyl-N-cyclohexylcarboxamido)benzyl]imidazo[4,5-c]pyridine | $10^{-7}$ | $10^{-6}$ | 2.82 |
| 5-[4-(N-3-pentyl-N-cyclohexylcarboxamido)benzyl]imidazo[4,5-c]pyridine | $10^{-7}$ to $10^{-8}$ | $10^{-6}$ $10^{-7}$ | — |
| 5-[4-(N-cyclopropyl-N-cyclohexylcarboxamido)benzyl]imidazo[4,5-c]pyridine | $10^{-6}$ to $10^{-7}$ | | 3.68 |
| 5-[4-(N-cyclobutyl-N-cyclohex,ylcarboxamido)benzyl]imidazo[4,5-c]pyridine | $10^{-8}$ to $10^{-9}$ | $10^{-7}$ to $10^{-8}$ | 0.0199 |
| 5-[4-(N-cyclopentyl-N-cyclohexylcarboxamido)benzyl]imidazo[4,5-c]pyridine | $10^{-8}$ to $10^{-9}$ | $10^{-7}$ to $10^{-8}$ | 0.32 |
| 5-(4-(N,N-dicyclohexyl carboxamidobenzyl)imidazo[4,5-c]pyridine | $10^{-8}$ | $10^{-6}$ to $10^{-7}$ | 1.06 |
| 5-[2-[4-(N-methyl-N-cyclohexylcarboxamido)phenyl]ethyl]imidazo[4,5-c]pyridine | $10^{-5}$ to $10^{-6}$ | $10^{-4}$ to $10^{-5}$ | — |
| 5-[3-[4-(N-methyl-N-cyclohexylcarboxamido)phenyl]propyl]imidazo[4,5-c]pyridine | $10^{-5}$ to $10^{-6}$ | $10^{-4}$ to $10^{-5}$ | 61.1 |
| 5-[4-(N,N-dicyclopentyl carboxamido)-2-methoxybenzyl]imidazo[4,5-c]pyridine | $10^{-8}$ to $10^{-9}$ | $10^{-7}$ to $10^{-8}$ | 0.055 |
| 5-[4-(N-cyclohexyl-N-cyclopentylcarboxamido)-2-methoxybenzyl]imidazo[4,5-c]pyridine | $10^{-8}$ to $10^{-9}$ | $10^{-8}$ | 0.0302 |
| 5-[4-(N-isopropyl-N-cyclohexylcarboxamido)2-methoxybenzyl]imidazo[4,5-c]pyridine | $10^{-8}$ | $10^{-7}$ to $10^{-8}$ | 0.0665 |
| 5-[4-(N-methyl-N-cyclohexyl carboxamido)-2-methoxybenzyl]imidazo[4,5-c]pyridine | $10^{-6}$ to $10^{-7}$ | $10^{-5}$ to $10^{-6}$ | — |
| 5-[4-(N-cyclopentyl-N-cyclohexylcarboxamido)-2-fluorobenzyl]imidazo[4,5-c]pyridine | $10^{-8}$ to $10^{-9}$ | $10^{-7}$ to $10^{-8}$ | 0.0755 |
| 5-[4-(N-isopropyl-N-cyclohexyl carboxamido)-2-fluorobenzyl] | $10^{-7}$ to $10^{-8}$ | $10^{-7}$ to $10^{-8}$ | 0.442 |

-continued

| Compound | PAF induced platelet secretion (IC$_{50}$)M | PAF induced platelet aggregation (IC$_{50}$)M | Inhibition of $^3$H-PAF Binding to Human Platelet (IC$_{50}$)μM |
|---|---|---|---|
| imidazo[4,5-c]pyridine | | | |
| 5-[4-(N-methyl-N-cyclohexyl carboxamido)-2-fluorobenzyl] imidazo[4,5-c]pyridine | $10^{-6}$ to $10^{-7}$ | $10^{-5}$ to $10^{-6}$ | — |
| 5-[4-(N-tert.butyl-N-cyclohexylcarboxamido) benzyl]imidazo[4,5-c]pyridine | $10^{-8}$ to $10^{-9}$ | $10^{-7}$ to $10^{-8}$ | 87.7% inhib (50 μM) |
| 5-[4-(N-phenyl-N-cyclopentylcarboxamido) benzyl]imidazo[4,5-c]pyridine | $10^{-6}$ to $10^{-7}$ | $10^{-6}$ | 2.35 |
| 5-[4-(N-3-methylcyclohexyl-N-cyclopentylcarboxamido)benzyl] imidazo[4,5-c]pyridine | $10^{-8}$ to $10^{-9}$ | $10^{-7}$ to $10^{-8}$ | 0.074 |
| 5-[4-(N-4-methylcyclohexyl-N-cyclopentylcarboxamido)benzyl] imidazo[4,5-c]pyridine | $10^{-7}$ to $10^{-8}$ | $10^{-6}$ to $10^{-7}$ | 0.75 |
| 5-[3-(N-methyl-N-cyclohexyl carboxamido)benzyl]imidazo[4,5-c]pyridine | $10^{-4}$ to $10^{-5}$ | $10^{-4}$ to $10^{-5}$ | 38% inhib (50 μM) |
| 5-[3-(N-isopropyl-N-cyclohexyl carboxamido)benzyl]imidazo[4,5-c]pyridine | $10^{-5}$ to $10^{-6}$ | $10^{-4}$ to $5 \times 10^{-5}$ | 26.1% inhib (50 μM) |
| 5-[4-(N,N-dicyclopentyl carboxamido)benzyl]-4-methylimidazo[4,5-c]pyridine | $10^{-7}$ to $10^{-8}$ | $10^{-7}$ to $10^{-8}$ | 0.188 |
| 5-[4-(N,N-dicyclopentyl carboxamido)benzyl]-2-methylimidazo[4,5-c]pyridine | $10^{-6}$ to $10^{-7}$ | $10^{-5}$ to $10^{-6}$ | 70.8% inhib (50 μM) |

What is claimed is:

1. A compound of the formula

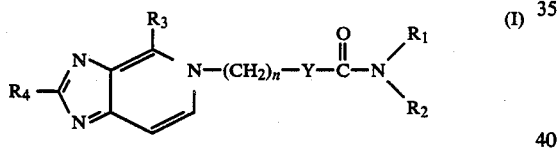

or a pharmaceutically acceptable acid addition salt thereof: wherein
R$_1$ and R$_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; bicycloalkyl having 3 to 8 carbon atoms in each ring; phenyl; substituted phenyl wherein the substituent is alkyl of 1 to 6 carbon atoms or halogen; straight or branched alkenyl having 3 to 15 carbon atoms with the proviso that the double bond of the alkenyl group cannot be adjacent to the nitrogen; R$_1$ and R$_2$ cannot both be hydrogen,
Y is phenyl or phenyl substituted once or more than by substituents selected from the group consisting of halogen wherein the halogen is selected from the group consisting of bromo, fluoro or chloro; alkyl of 1 to 6 carbon atoms; alkoxy wherein the alkyl is 1 to 6 carbon atoms; thioalkyl wherein the alkyl is 1 to 6 carbon atoms; alkoxyalkyl wherein the alkyl groups are each 1 to 6 carbon atoms; hydroxyalkyl wherein the alkyl is 1 to 6 carbon atoms; alkylthioalkyl wherein the alkyl group are each 1 to 6 carbon atoms; cyano; mercaptoalkyl wherein the alkyl is 1 to 6 carbon atoms; hydroxy, substituents on the phenyl ring can be ortho, para, or meta to the connecting chain, depending on the position of the carboxamide,
n is an integer of 1 to 5,
R$_3$ is hydrogen or alkyl of 1 to 6 carbon atoms,
R$_4$ is hydrogen or alkyl of 1 to 6 carbon atoms.

2. A compound according to claim 1 having the formula

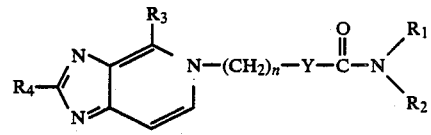

or a pharmaceutically acceptable acid addition salt thereof: wherein
R$_1$ and R$_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; bicycloalkyl having 3 to 8 carbon atoms in each ring; phenyl; substituted phenyl wherein the substituent is alkyl of 1 to 6 carbon atoms or halogen; straight or branched alkenyl having 3 to 15 carbon atoms with the proviso the double bond of the alkenyl group cannot be adjacent to the nitrogen; R$_1$ and R$_2$ cannot both be hydrogen,
Y is phenyl; substituted phenyl wherein the substituent is halogen selected from the group consisting of bromo, fluoro or chloro; or alkoxy wherein the alkyl is 1 to 6 carbon atoms, Substituents on the phenyl ring can be ortho, para, or meta to the connecting chain, depending on the position of the carboxamide,
n is an integer of 1 to 5, R₃ is hydrogen or alkyl of 1 to 6 carbon atoms,
R₄ is hydrogen or alkyl of 1 to 6 carbon atoms.

3. A compound according to claim 2 wherein R₁ and R₂ are each independently selected from hydrogen; straight or branched chain alkyl of 1 to 15 carbon atoms; cycloalkyl having 3 to 8 carbon atoms; bicycloalkyl having 3 to 8 carbon atoms in each ring; or phenyl.

4. A compound according to claim 3 wherein R₁ and R₂ are each independently selected from hydrogen; straight or branched chain alkyl of 1 to 15 carbon atoms; or cycloalkyl having 3 to 8 carbon atoms.

5. A compound according to claim 2 where Y is phenyl.

6. A compound according to claim 2 wherein Y is substituted phenyl wherein the substituent is halogen selected from the group consisting of bromo, fluoro, or chloro or alkoxy wherein the alkyl is 1 to 6 carbon atoms.

7. A compound according to claim 6 wherein the halogen is fluoro.

8. A compound according to claim 6 wherein the alkoxy is methoxy.

9. A compound according to claim 2 wherein n is an integer of 1 to 3.

10. A compound according to claim 1 having the formula

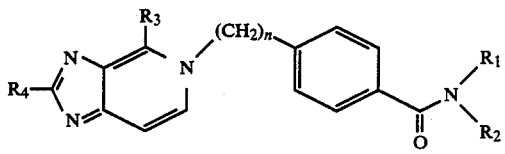

or a pharmaceutically acceptable acid addition salt thereof: wherein R₁ and R₂ are each independently selected from hydrogen; straight or branched chain alkyl of 1 to 15 carbon atoms; cycloalkyl having 3 to 8 carbon atoms; bicycloalkyl having 3 to 8 carbon atoms in each ring; or phenyl, n is an integer of 1 to 3, R₃ is hydrogen or alkyl of 1 to 6 carbon atoms and R₄ is hydrogen or alkyl of 1 to 6 carbon atoms.

11. A compound according to claim 10 which is 5-[4-(N-methyl-N-cyclohexylcarboxamido)benzyl]imidazo[4,5-c]pyridine.

12. A compound according to claim 10 which is 5-[4-(N-n-octylcarboxamido)benzyl]imidazo[4,5-c]pyridine.

13. A compound according to claim 10 which is 5-[4-(N-n-decylcarboxamido)benzyl]imidazo[4,5-c]pyridine.

14. A compound according to claim 10 which is 5-[4-(N-n-dodecylcarboxamido)benzyl]imidazo[4,5-c]pyridine.

15. A compound according to claim 10 which is 5-[4-(N-2-decalyl-N-methylcarboxamido)benzyl]imidazo[4,5-c]pyridine.

16. A compound according to claim 10 which is 5-[4-(N-2-(2,4,4-trimethyl)pentylcarboxamido)benzyl]imidazo[4,5-c]pyridine.

17. A compound according to claim 10 which is 5-[4-(N,N-diisopropylcarboxamido)benzyl]imidazo[4,5-c]pyridine.

18. A compound according to claim 10 which is 5-[4-(N,N-dicyclopentylcarboxamido)benzyl]imidazo[4,5-c]pyridine.

19. A compound according to claim 10 which is 5-[4-(N-cyclohexylcarboxamido)benzyl]imidazo[4,5-c]pyridine.

20. A compound according to claim 10 which is 5-[4-(N-ethyl-N-cyclohexylcarboxamido)benzyl]imidazo[4,5-c]pyridine.

21. A compound according to claim 10 which is 5-[4-(N-isopropyl-N-cyclohexylcarboxamido)benzyl]imidazo[4,5-c]pyridine.

22. A compound according to claim 10 which is 5-[4-(N-sec.butyl-N-cyclohexylcarboxamido)benzyl]imidazo[4,5-c]pyridine.

23. A compound according to claim 10 which is 5-[4-(N-isobutyl-N-cyclohexylcarboxamido)benzyl]imidazo[4,5-c]pyridine.

24. A compound according to claim 10 which is 5-[4-(N-3-pentyl-N-cyclohexylcarboxamido)benzyl]imidazo[4,5-c]pyridine.

25. A compound according to claim 10 which is 5-[4-(N-cyclopropyl-N-cyclohexylcarboxamido)benzyl]imidazo[4,5-c]pyridine.

26. A compound according to claim 10 which is 5-[4-(N-cyclobutyl-N-cyclohexylcarboxamido)benzyl]imidazo[4,5-c]pyridine.

27. A compound according to claim 10 which is 5-[4-(N-cyclopentyl-N-cyclohexylcarboxamido)benzyl]imidazo[4,5-c]pyridine.

28. A compound according to claim 10 which is 5-(4-(N,N-dicyclohexylcarboxamidobenzyl)imidazo[4,5-c]pyridine.

29. A compound according to claim 10 which is 5-[2-[4-(N-methyl-N-cyclohexylcarboxamido)phenyl]ethyl]imidazo[4,5-c]pyridine.

30. A compound according to claim 10 which is 5-[3-[4-(N-methyl-N-cyclohexylcarboxamido)phenyl]propyl]imidazo[4,5-c]pyridine.

31. A compound according to claim 10 which is 5-[4-(N-tert.butyl-N-cyclohexylcarboxamido)benzyl]imidazo[4,5-c]pyridine.

32. A compound according to claim 10 which is 5-[4-(N-phenyl-N-cyclopentylcarboxamido)benzyl]imidazo[4,5-c]pyridine.

33. A compound according to claim 10 which is 5-[4-(N-3-methylcyclohexyl-N-cyclopentylcarboxamido)benzyl]imidazo[4,5-c]pyridine.

34. A compound according to claim 10 which is 5-[4-(N-4-methylcyclohexyl-N-cyclopentylcarboxamido)benzyl]imidazo[4,5-c]pyridine.

35. A compound according to claim 10 which is 5-[4-(N,N-dicyclopentylcarboxamido)benzyl]-2-methylimidazo[4,5-c]pyridine.

36. A compound according to claim 10 which is 5-[4-(N,N-dicyclopentylcarboxamido)benzyl]-4-methylimidazo[4,5-c]pyridine.

37. A compound according to claim 10 which is 5-[3-(N-methyl-N-cyclohexylcarboxamido)benzyl]imidazo[4,5-c]pyridine.

38. A compound according to claim 10 which is 5-[3-(N-isopropyl-N-cyclohexylcarboxamido)benzyl]imidazo[4,5-c]pyridine.

39. A compound according to claim 1 wherein R₁ and R₂ are each independently selected from hydrogen; straight or branched chain alkyl of 1 to 15 carbon atoms; cycloalkyl having 3 to 8 carbon atoms; bicycloalkyl having 3 to 8 carbon atoms in each ring or phenyl, Y is substituted phenyl wherein the substituent is halogen selected from the group consisting of bromo, fluoro, or chloro or alkoxy wherein the alkyl is 1 to 6 carbon atoms, n is an integer of 1 to 3, $R_3$ is hydrogen or alkyl of 1 to 6 carbon atoms and $R_4$ is hydrogen or alkyl of 1 to 6 carbon atoms.

40. A compound according to claim 39 wherein the halogen is fluoro.

41. A compound according to claim 40 which is 5-[4-(N-cyclopentyl-N-cyclohexylcarboxamido)-2-fluorobenzyl]imidazo[4,5-c]pyridine.

42. A compound according to claim 40 which is 5-[4-(N-isopropyl-N-cyclohexylcarboxamido)-2-fluorobenzyl]imidazo[4,5-c]pyridine.

43. A compound according to claim 40 which is 5-[4-(N-methyl-N-cyclohexylcarboxamido)-2-fluorobenzyl]imidazo[4,5-c]pyridine.

44. A compound according to claim 39 wherein the alkoxy is methoxy.

45. A compound according to claim 44 which is 5-[4-(N,N-dicyclopentylcarboxamido)-2-methoxybenzyl]imidazo[4,5-c]pyridine.

46. A compound according to claim 44 which is 5-[4-(N-cyclohexyl-N-cyclopentylcarboxamido)-2-methoxybenzyl]imidazo[4,5-c]pyridine.

47. A compound according to claim 44 which is 5-[4-(N-isopropyl-N-cyclohexylcarboxamido)-2-methoxybenzyl]imidazo[4,5-c]pyridine.

48. A compound according to claim 44 which is 5-[4-(N-methyl-N-cyclohexylcarboxamido)-2-methoxybenzyl]imidazo[4,5-c]pyridine.

49. A pharmaceutical composition useful for treating diseases or disorder mediated by platelet-activating factor comprising at least one compound according to claim 1, together with one or more non-toxic pharmaceutically acceptable carriers.

50. A pharmaceutical composition according to claim 49 wherein said compound is selected from the group consisting of 5-[4-(N-methyl-N-cyclohexylcarboxamido)benzyl]imidazo[4,5-c]pyridine 5-[4-(N-n-octylcarboxamido)benzyl]imidazo[4,5-c]pyridine 5-[4-(N-n-decylcarboxamido)benzyl]imidazo[4,5-c]pyridine 5-[4-(N-n-dodecylcarboxamido)benzyl]imidazo[4,5-c]pyridine 5-[4-(N-2-decalyl-N-methylcarboxamido)benzyl]imidazo[4,5-c]pyridine 5-[4-(N-2-(2,4,4-trimethyl)pentylcarboxamido)benzyl]imidazo[4,5-c]pyridine 5-[4-(N,N-diisopropylcarboxamido)benzyl]imidazo[4,5-c]pyridine 5-[4-(N,N-dicyclopentylcarboxamido)benzyl]imidazo[4,5-c]pyridine 5-[4-(N-cyclohexylcarboxamido)benzyl]imidazo[4,5-c]pyridine 5-[4-(N-ethyl-N-cyclohexylcarboxamido)benzyl]imidazo[4,5-c]pyridine 5-[4-(N-isopropyl-N-cyclohexylcarboxamido)benzyl]imidazo[4,5-c]pyridine 5-[4-(N-sec.butyl-N-cyclohexylcarboxamido)benzyl]imidazo[4,5-c]pyridine 5-[4-(N-isobutyl-N-cyclohexylcarboxamido)benzyl]imidazo[4,5-c]pyridine 5-[4-(N-3-pentyl-N-cyclohexylcarboxamido)benzyl]imidazo[4,5c]pyridine 5-[4-(N-cyclopropyl-N-cyclohexylcarboxamido)benzyl]imidazo[4,5-c]pyridine 5-[4-(N-cyclobutyl-N-cyclohexylcarboxamido)benzyl]imidazo[4,5-c]pyridine 5-[4-(N-cyclopentyl-N-cyclohexylcarboxamido)benzyl]imidazo[4,5-c]pyridine 5-(4-(N,N-dicyclohexylcarboxamidobenzyl)imidazo[4,5-c]pyridine 5-[2-[4-(N-methyl-N-cyclohexylcarboxamido)phenyl]ethyl]imidazo[4,5-c]pyridine 5-[3-[4-(N-methyl-N-cyclohexylcarboxamido)phenyl]propyl]imidazo[4,5-c]pyridine 5-[4-(N-tert.butyl-N-cyclohexylcarboxamido)benzyl]imidaizo[4,5-c]pyridine 5-[4-(N-phenyl-N-cyclopentylcarboxamido)benzyl]imidazo[4,5-c]pyridine 5-[4-(N-3-methylcyclohexyl-N-cyclopentylcarboxamido)benzyl]imidazo[4,5-c]pyridine 5-[4-(N-4-methylcyclohexyl-N-cyclopentylcarboxamido)benzyl]imidazo[4,5-c]pyridine 5-[4-(N,N-dicyclopentylcarboxamido)-2-methoxybenzyl]imidazo[4,5-c]pyridine 5-[4-(N-cyclohexyl-N-cyclopentylcarboxamido)-2-methoxybenzyl]imidazo[4,5-c]pyridine 5-[4-(N-isopropyl-N-cyclohexylcarboxamido)-2-methoxybenzyl]imidazo[4,5-c]pyridine 5-[4-(N-methyl-N-cyclohexylcarboxamido)-2-methoxybenzyl]imidazo[4,5-c]pyridine 5-[4-(N-cyclopentyl-N-cyclohexylcarboxamido)-2-fluorobenzyl]imidazo[4,5-c]pyridine 5-[4-(N-isopropyl-N-cyclohexylcarboxamido)-2-fluorobenzyl]imidazo[4,5-c]pyridine 5-[4-(N-methyl-N-cyclohexylcarboxamido)-2-fluorobenzyl]imidazo[4,5-c]pyridine 5-[3-(N-methyl-N-cyclohexylcarboxamido)benzyl]imidazo[4,5-c]pyridine 5-[3-(N-isopropyl-N-cyclohexylcarboxamido)benzyl]imidazo[4,5-c]pyridine 5-[4-(N,N-dicyclopentylcarboxamido)benzyl]-4-methylimidazo[4,5-c]pyridine and 5-[4-(N,N-dicyclopentylcarboxamido)benzyl]-2-methylimidazo[4,5-c]pyridine.

51. A method for treating diseases or disorder mediated by platelet-activating factor comprising administering a therapeutically effective dose of at least one compound of claim 1 to a mammal in need of such treatment.

52. A method according to claim 51 wherein said compound is selected from the group consisting of 5-[4-(N-methyl-N-cyclohexylcarboxamido)benzyl]imidazo[4,5-c]pyridine 5-[4-(N-n-octylcarboxamido)benzyl]imidazo[4,5-c]pyridine 5-[4-(N-n-decylcarboxamido)benzyl]imidazo[4,5-c]pyridine 5-[4-(N-n-dodecylcarboxamido)benzyl]imidazo[4,5-c]pyridine 5-[4-(N-2-decalyl-N-methylcarboxamido)benzyl]imidazo[4,5-c]pyridine 5-[4-(N-2-(2,4,4-trimethyl)pentylcarboxamido)benzyl]imidazo[4,5-c]pyridine 5-[4-(N,N-diisopropylcarboxamido)benzyl]imidazo[4,5-c]pyridine 5-[4-(N,N-dicyclopentylcarboxamido)benzyl]imidazo[4,5-c]pyridine 5-[4-(N-cyclohexylcarboxamido)benzyl]imidazo[4,5-c]pyridine 5-[4-(N-ethyl-N-cyclohexylcarboxamido)benzyl]imidazo[4,5-c]pyridine 5-[4-(N-isopropyl-N-cyclohexylcarboxamido)benzyl]imidazo[4,5-c]pyridine 5-[4-(N-sec.butyl-N-cyclohexylcarboxamido)benzyl]imidazo[4,5-c]pyridine
5-[4-(N-isobutyl-N-cyclohexylcarboxamido)benzyl]imidazo[4,5-c]pyridine
5-[4-(N-3-pentyl-N-cyclohexylcarboxamido)benzyl]imidazo[4,5-c]pyridine
5-[4-(N-cyclopropyl-N-cyclohexylcarboxamido)benzyl]imidazo[4,5-c]pyridine
5-[4-(N-cyclobutyl-N-cyclohexylcarboxamido)benzyl]imidazo[4,5-c]pyridine
5-[4-(N-cyclopentyl-N-cyclohexylcarboxamido)benzyl]imidazo[4,5-c]pyridine
5-(4-(N,N-dicyclohexylcarboxamidobenzyl)imidazo[4,5-c]pyridine
5-[2-[4-(N-methyl-N-cyclohexylcarboxamido)phenyl]ethyl]imidazo[4,5-c]pyridine
5-[3-[4-(N-methyl-N-cyclohexylcarboxamido)phenyl]propyl]imidazo[4,5-c]pyridine
5-[4-(N-tert.butyl-N-cyclohexylcarboxamido)benzyl]imidazo[4,5-c]pyridine
5-[4-(N-phenyl-N-cyclopentylcarboxamido)benzyl]imidazo[4,5-c]pyridine
5-[4-(N-3-methylcyclohexyl-N-cyclopentylcarboxamido)benzyl]imidazo[4,5-c]pyridine
5-[4-(N-4-methylcyclohexyl-N-cyclopentylcarboxamido)benzyl]imidazo[4,5-c]pyridine
5-[4-(N,N-dicyclopentylcarboxamido)-2-methoxybenzyl]imidazo[4,5-c]pyridine
5-[4-(N-cyclohexyl-N-cyclopentylcarboxamido)-2-methoxybenzyl]imidazo[4,5-c]pyridine
5-[4-(N-isopropyl-N-cyclohexylcarboxamido)-2-methoxybenzyl]imidazo[4,5-c]pyridine
5-[4-(N-methyl-N-cyclohexylcarboxamido)-2-methoxybenzyl]imidazo[4,5-c]pyridine
5-[4-(N-cyclopentyl-N-cyclohexylcarboxamido)-2-fluorobenzyl]imidazo[4,5-c]pyridine
5-[4-(N-isopropyl-N-cyclohexylcarboxamido)-2-fluorobenzyl]imidazo[4,5-c]pyridine
5-[4-(N-methyl-N-cyclohexylcarboxamido)-2-fluorobenzyl]imidazo[4,5-c]pyridine
5-[3-(N-methyl-N-cyclohexylcarboxamido)benzyl]imidazo[4,5-c]pyridine
5-[3-(N-isopropyl-N-cyclohexylcarboxamido)benzyl]imidazo[4,5-c]pyridine
5-[4-(N,N-dicyclopentylcarboxamido)benzyl]-4-methylimidazo[4,5-c]pyridine and
5-[4-(N,N-dicyclopentylcarboxamido)benzyl]-2-methylimidazo[4,5-c]pyridine.

53. A method for treating diseases or disorder mediated by platelet-activating factor comprising administering a therapeutically effective dose of pharmaceutical composition of claim 49 to mammal in need of such treatment.

* * * * *